(12) United States Patent
Cros et al.

(10) Patent No.: US 10,168,270 B2
(45) Date of Patent: Jan. 1, 2019

(54) SAMPLE HOLDER AND ASSOCIATED PERMEATION DEVICE

(71) Applicant: COMMISSARIAT A L'ENERGIE ATOMIQUE ET AUX ENERGIES ALTERNATIVES, Paris (FR)

(72) Inventors: Stéphane Cros, Chambery (FR); Jean-Philippe Fauvarque, L'Etang la Ville (FR); Arnaud Leroy, Chambery (FR); Christine Walsh, Clichy (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 194 days.

(21) Appl. No.: 15/030,129

(22) PCT Filed: Nov. 24, 2014

(86) PCT No.: PCT/FR2014/053012
§ 371 (c)(1),
(2) Date: Apr. 18, 2016

(87) PCT Pub. No.: WO2015/079151
PCT Pub. Date: Jun. 4, 2015

(65) Prior Publication Data
US 2016/0266024 A1    Sep. 15, 2016

(30) Foreign Application Priority Data
Nov. 26, 2013  (FR) .................................... 13 61658

(51) Int. Cl.
*G01N 15/08* (2006.01)

(52) U.S. Cl.
CPC ....... *G01N 15/0806* (2013.01); *G01N 15/082* (2013.01)

(58) Field of Classification Search
CPC . G01N 15/0806; G01N 15/082; G01N 15/084
(Continued)

(56) References Cited

U.S. PATENT DOCUMENTS 4,531,404 A    7/1985  Phelps et al.
5,659,130 A    8/1997  Chung et al.
(Continued)

FOREIGN PATENT DOCUMENTS

FR          2715471 A1     7/1995

OTHER PUBLICATIONS

International Search Report issued in PCT/FR2014/053012 dated Feb. 5, 2015.

*Primary Examiner* — Robert R Raevis
(74) *Attorney, Agent, or Firm* — Marshall, Gerstein & Borun LLP (57) ABSTRACT

A cell for measuring the permeation of a target gas through a sample includes upstream and downstream chambers connected by an opening, a primary seal in contact with the bottom of the upstream chamber and surrounding the opening, and a removable sample holder and means for assembling the sample holder in the cell. Upper and lower frames included in the sample holder are each provided with a through opening. The sample holder includes means for assembling the sample in the sample holder and a first seal flush with the front surface of the lower frame, and surrounding the through opening of the lower frame. In the lower frame of the sample holder, a second seal is flush with the front surface of the lower frame, surrounding the through opening of the lower frame, and being surrounded with the first seal, and a second channel emerging between the two secondary seals.

12 Claims, 6 Drawing Sheets

(58) Field of Classification Search
USPC .................. 73/38, 864.91, 863.23, 863.25
See application file for complete search history.

(56) References Cited

U.S. PATENT DOCUMENTS

| | | | |
|---|---|---|---|
| 5,979,223 | A | 11/1999 | Fleury |
| 7,624,621 | B2 | 12/2009 | Firon et al. |
| 8,388,742 | B2 | 3/2013 | Nunes |
| 2006/0236755 | A1 | 10/2006 | Bujas et al. |
| 2010/0054998 | A1 | 3/2010 | Mayer et al. |
| 2010/0268488 | A1* | 10/2010 | Bismarck ............ G01N 15/0826 702/50 |
| 2011/0168023 | A1* | 7/2011 | Nunes ................. B01D 65/003 96/4 |

* cited by examiner

Fig. 1
ART ANTERIEUR

Fig. 2
ART ANTERIEUR

SAMPLE HOLDER AND ASSOCIATED PERMEATION DEVICE

CROSS-REFERENCE TO RELATED APPLICATIONS

This application is a national stage application under 35 U.S.C. § 371 and claims the benefit of priority of international application no. PCT/FR2014/053012, filed Nov. 24, 2014, which claims the benefit of priority under 35 U.S.C. § 119 of French patent application no. 1361658, filed Nov. 26, 2013, and the entire contents of each is hereby incorporated herein by reference, in its entirety and for all purposes.

TECHNOLOGY FIELD

The present disclosure relates to measurements of the permeability of a sample and, more specifically, to a permeation cell comprising a removable sample holder.

BACKGROUND

Electronic components and photovoltaic panels based on organic materials are particularly sensitive to oxidation phenomena created by water and dioxygen. To be able to increase the lifetime of such elements, it is necessary to protect them with a film which is as little permeable as possible to oxidizing gases.

Permeability measurements are expressed in water vapor transmission rate (WVTR). Such measurements express the quantity of gas orthogonally crossing the film surface per day ($g \cdot m^{-2} \cdot d^{-1}$). The most impermeable or the best barrier films have a WVTR value in the order of $10^{-6}$ $g \cdot m^{-2} \cdot d^{-1}$.

Figure 1:
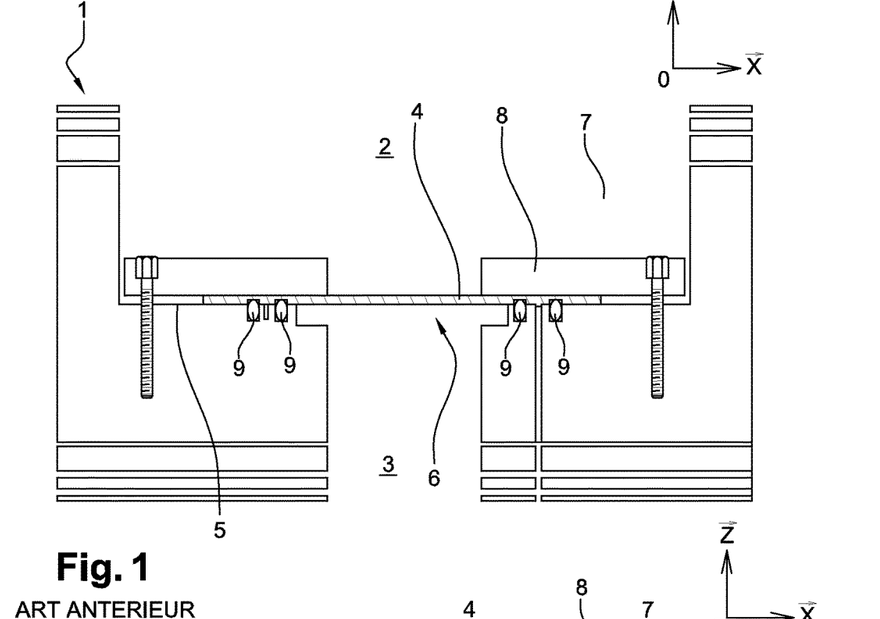
FIG. 1 is a simplified front view of a permeation cell according to the state of the art.

To perform this type of measurement and referring to FIG. 1, a protective film or sample is placed in a permeation cell (1), comprising an upstream chamber (2) and a downstream chamber (3). More specifically, the sample (4) is held close to the bottom (5) of the upstream chamber to close an opening (6) connecting the two chambers. After being closed with a cover, the upstream chamber is filled with a target gas (7), for example, water vapor. The downstream chamber (3) has a detection device (not shown) capable of detecting the gas present in the downstream chamber (3), and accordingly having diffused from the upstream chamber (2) through the sample (4), arranged therein.

Permeation device examples are described in documents U.S. Pat. No. 7,624,621 and U.S. Pat. No. 8,388,742.

Due to the importance of the signal-to-noise ratio to perform high-sensitivity measurements, the phenomenon of contamination of the downstream chamber with the target gas on installation of the sample is critical. Such a contamination phenomenon essentially comprises the adsorption of gas by the walls of the downstream chamber. To obtain a quality measurement, the gas present in the downstream chamber should only result from the diffusion through the sample and be able to be distinguished from the noise originating from the desorption of the gases having contaminated the downstream chamber.

The installing of the sample in the downstream chamber (2) requires an opening of the permeation cell, and thus an exposure of the chambers to the atmosphere, as well as touchy and long manipulations to correctly close the opening (6) with the sample (4). The manipulation time may in particular be related to the steps of installing the sample and of tightening seals ensuring the tightness between the sample (4) and the bottom (5) of the downstream chamber. During this operation, as long as the upstream chamber (2) is not closed, the upstream and downstream chambers are contaminated by the atmosphere. To allow fine measurements of permeability to gas species present in the atmosphere, it is then necessary to purge with a neutral gas or to create a high vacuum in the downstream chamber containing the detection device before performing the measurement to decontaminate as much as possible the downstream chamber and thus decrease the noise corresponding to the measurement target gas. The purging or pump-out time enabling to obtain a given background noise is all the longer as the time of opening to the atmosphere to install the sample is long. Thereby, high-sensitivity permeability measurements for which the background noise should be low currently require a long decontamination time in the downstream chamber, which accordingly lengthens the total measurement time.

Even though the downstream chamber contamination would only slightly impact the measurement sensitivity, certain detection devices however require a high vacuum in the downstream chamber to be able to operate. This is particularly true when the detection device is a mass spectrometer for which it is necessary to reach a sufficiently high vacuum level to be able to use it.

Now, the downstream chamber purging or pump-out time is also strongly connected to the time of contamination of the downstream chamber by the atmosphere and accordingly impacts the total time of an experiment. Thus, if fast measurements are successively performed over a large number of samples, as in the case of the helium permeation detection device described in U.S. Pat. No. 7,624,621, the time necessary to drain the downstream chamber after each change of sample may become longer than the measurement time and considerably lengthen the total time of the experiment.

Another disadvantage of current permeation cells relates to the holding of the sample (4) at the level of the opening (6) connecting the two chambers (2) (3). Generally, the sample (4) is sealed on the opening (6) by a frame (8) screwed to the bottom of the upstream chamber, which presses the sample against said bottom (FIG. 1). The frame thus exerts mechanical stress on the sample, capable of deteriorating it, for example, by deforming its structure or by scratching its surface, particularly at the level of the contact with the seals (9). Thereby, permeation measurements are often considered as destructive for fragile films. Thereby, if the sample is measured a first time, and then taken out of the cell, a second measurement on the cell is a problem due to a serious doubt as to the damaging of the sample during the first measurement. Indeed, the positioning of the sample in the cell is generally not very accurate, so that its installing in a cell may be performed in a configuration which differs from that of the first measurement. The above-mentioned deteriorations may thus be present at the level of the surface exposed to the target gas during the second measurement, which alters the measurement.

Further, the manipulation of a sample always induces a doubt as to the preservation of its integrity. Indeed, for example, the above-mentioned protective films have a decreased thickness and the manipulation of such films is usually very delicate.

Thus, a sample measured a first time is not considered to date as having kept a sufficient integrity to be measured a second time. This strongly limits its study in different conditions (particularly climatic conditions).

Figure 2:
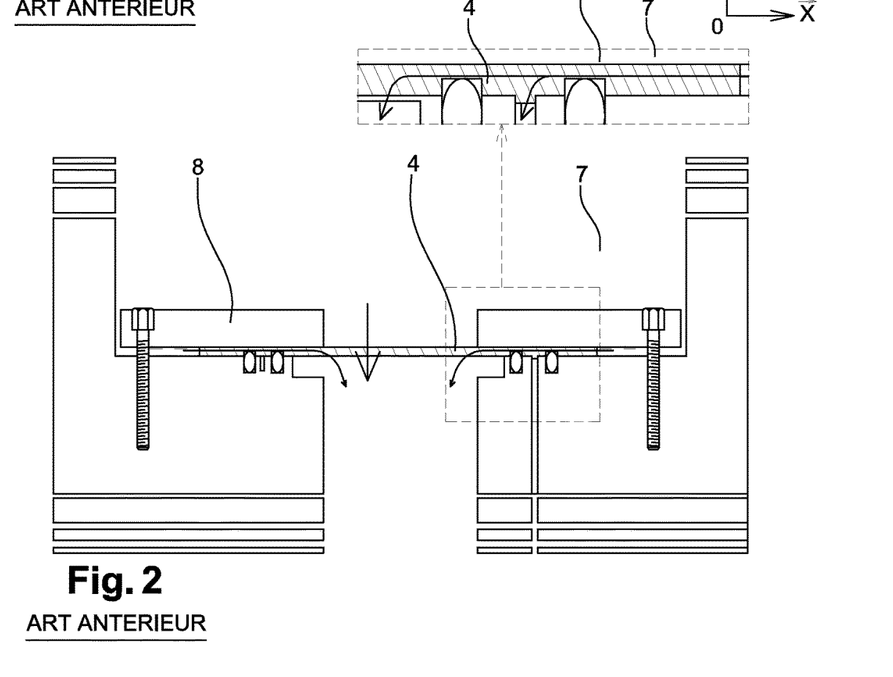
FIG. 2 is another simplified front view of a permeation cell according to the state of the art, illustrating the lateral permeation phenomenon.

Another disadvantage linked to permeation cells of the state of the art is the phenomenon of lateral permeation along axis x such as shown in FIG. 2, that is, in the sample plane. A permeation measurement theoretically comprises measuring the flow of a target gas orthogonally crossing the sample, that is, along axis z such as shown in FIG. 2. Theoretically, the frame (8) enables to accurately define the surface of the sample in contact with the target gas. In practice, for samples comprising layers of different permeability, the target gas (7) may laterally diffuse into the less permeable layers. This for example occurs for films comprising a plastic substrate, forming a weak barrier against gases, covered with a dense organic layer, forming a strong barrier against gases. The surface of the sample exposed to the target gas thus no longer corresponds to that defined by the frame. Thereby, the measurements may be altered if the lateral permeation is not negligible as compared with the orthogonal permeation.

SUMMARY OF THE DISCLOSURE

The presently disclosed embodiments provide a permeation cell enabling to reproducibly position the sample in the cell, while preserving the integrity of the sample portion placed in the passage connecting the two cell chambers.

The present application aims at solving the above-mentioned technical problem, by providing a permeation cell capable of measuring the permeation of a target gas through a sample. In one embodiment, the permeation cell includes an upstream chamber capable of containing the target gas and delimited by a bottom, and a downstream chamber capable of being in fluidic communication with a target gas detection device. The permeation cell also includes an opening connecting the downstream chamber to the upstream chamber and emerging into the bottom of the upstream chamber, a first so-called primary seal in contact with the bottom of the upstream chamber and surrounding the opening, and means for fixing the sample at the bottom of the upstream chamber.

The fixing means of the permeation cell may include a removable sample holder, which sample holder includes an upper frame provided with a front surface and with a rear surface connected by a through opening, and a lower frame, capable of being taken away from the upper frame, provided with a front surface and with a rear surface connected by a through opening. The sample holder also includes means for assembling the sample holder. The means for assembling the sample holder are settable between an assembled state of the sample holder where the rear surface of the upper frame and the front surface of the lower frame are pressed towards each other with the openings of the upper and lower frames facing each other, to keep the sample in the sample holder opposite said openings, and a disassembled state of the sample holder where the upper and lower frames are capable of being taken away from each other to allow the installing and the retrieval of the sample from the sample holder. The sample holder further includes means for assembling the cell which means are settable between a state where the rear surface of the lower frame of the sample holder is pressed against the first primary seal and a state where the sample holder is free.

As used herein, the term "opening" means a passage between two areas enabling a fluid to pass between said areas. As used herein, the term "primary seal" means one or a plurality of seals belonging to a same group called "primary group".

The cell assembly means advantageously enable to press the rear surface of the lower frame of the sample holder against the first primary seal, to prevent a fluid present in the upstream chamber from reaching the downstream chamber by passing between the rear surface of the lower frame and the bottom of the upstream chamber. In other words, a fluid originating from the upstream chamber may reach the downstream chamber only by passing through the opening crossing the lower frame.

To achieve this, the first primary seal advantageously has an O-ring shape to form a tight barrier all around the opening connecting the downstream chamber to the upstream chamber and between the rear surface of the lower frame and the bottom of the upstream chamber.

The sample holder assembly means advantageously enable to control the distance between the front surface of the lower frame and the rear surface of the upper frame, to possibly allow the frames to clamp a sample to close their respective opening. Thus, a target gas present in the upstream chamber may reach the downstream chamber only by passing through the sample, when the rear surface of the lower frame is pressed against the first primary seal in contact with the bottom of the downstream chamber.

Advantageously, the sample holder assembly means and the cell assembly means are distinct. Thereby, the sample may be placed in the sample holder before its introduction into the upstream chamber. The fixing of the sample to the bottom of the upstream chamber may also be performed faster via the second holding means. This enables to limit the time of opening and of contamination of the chambers of the permeation cell, and thus to significantly decrease the time necessary to prepare said cell before carrying out permeation measurements.

Another advantage of the removable sample holder is the possibility of installing the sample into and of taking it out of the upstream chamber without it being necessary, for this purpose, to directly manipulate the sample. Indeed, the sample may be easily retrieved from the upstream chamber by only manipulating the upper frame and/or the lower frame. Thus, on the one hand, it is made sure not to deteriorate the sample on installing thereof into and on removing it from the permeation cell, and on the other hand, one may be sure of identically repeating permeation measurements on a sample after having taken it out of the upstream chamber. Indeed, the frames are rigidly fastened to the sample by means of the sample holder assembly means, so that the sample holder and the sample can be placed in the desired conditions (photochemical aging, for example), and then measured against with no risk of mechanical alteration due to the manipulation of the sample. Further, the cell assembly means, for example, formed by means of screws, are also used as means for positioning the sample holder in the cell, the latter being placed in a specific known position, advantageously unique.

The assembly means may be formed in different ways. For example, the sample holder assembly means may comprise at least two screws crossing the front and rear surfaces of the upper frame and the front surface of the lower frame. The cell assembly means may for example comprise at least two screws crossing the front and rear surfaces of the upper and lower frames, said screws being screwed in dedicated housings, formed in the bottom of the upstream chamber. Of course, any other assembly or holding means carrying out the same functions may be envisaged. For example, the cell assembly means may be replaced with means enabling to press the front surface of the upper frame to hold the rear surface of the lower frame against the first primary seal.

According to a variation, the sample holder assembly means comprise at least one pin enabling to hold the two frames opposite each other, while possibly holding a sample therebetween.

According to a feature of one or more presently described embodiments, the upstream chamber may comprise a second so-called primary seal, in contact with the bottom of the upstream chamber and surrounding the opening connecting the downstream chamber to the upstream chamber. The second primary seal may be surrounded with the first primary seal. Thus, via a first channel emerging into the bottom of the upstream chamber, between the first and the second primary seals and connected to suction means, the fluid present between said seals may be pumped to provide a better tightness between the rear surface of the lower frame and the bottom of the upstream chamber to prevent any possible leak at the level of the first primary seal. This first channel may enable to advantageously introduce an inert gas between the seals to improve the tightness to the target gas.

To make sure that the pressure is homogeneous between the first and the second primary seals, a groove may advantageously be formed between the first and the second primary seals, and preferably all around the second primary seal.

According to another characteristic of the removable sample holder, a first so-called secondary seal may be flush with the front surface of the lower frame and surround the through opening of this frame. Term "secondary" means one or a plurality of seals belonging to a same so-called secondary group, to differentiate them from the seals belonging to the so-called primary group. The seals may be formed from an elastomer or metallic material.

The lower frame of the sample holder may include a second so-called secondary seal flush with the front surface of the lower frame and surrounding the through opening of the lower frame, the second secondary seal being surrounded with the first secondary seal. The lower frame may also include the front surface and the rear surface of the lower frame are connected by a second channel emerging between the two primary seals and between the two secondary seals.

The second channel, the primary and secondary seals may enable pumping means connected to the first channel to suck in a fluid present in the space defined between the secondary seals and the front surface of the lower frame. Thus, in the case where a sample is in contact with the secondary seals, the pumping means may improve the tightness between the sample and the lower frame to prevent the target gas from passing into the downstream chamber through this passage.

Possibly, to allow a more homogeneous suction into the area defined by the secondary seals, the second channel may comprise a groove formed on the front surface of the lower frame of the sample holder between the two secondary seals. Preferably, the groove surrounds the first secondary seal.

According to another feature of the permeation cell, the cell may comprise a third channel which emerges into the bottom of the upstream chamber between the first primary seal and a lateral wall delimiting the upstream chamber and its bottom. In other words, the upstream chamber is delimited by a bottom and a lateral wall defining the periphery of said bottom.

Advantageously, a third so-called primary seal may then be in contact with the upper frame of the sample holder and the lateral wall of the upstream chamber, to enable pumping means connected to the third channel to improve the tightness between the first and the third primary seals.

The sample holder may comprise a third so-called secondary seal flush with the rear surface of the upper frame and surrounding the through opening of the frame, to improve the tightness between the rear surface of the frame and a sample clamped between the lower and upper frame, to limit the above-mentioned lateral permeation phenomenon.

According to a variation, the permeation cell may include a third so-called primary seal in contact with the bottom of the upstream chamber and the rear surface of the lower frame of the sample holder, the fourth seal surrounding the third channel and the first primary seal. The sample holder may include a third so-called secondary seal flush with the rear surface of the upper frame and surrounding the through opening of the upper frame, a fourth so-called secondary seal in contact with the rear surface of the upper frame and the front surface of the lower frame, the fourth seal surrounding the third secondary seal, and a fourth channel emerging between the first and the fourth secondary seals and between the first and the third primary seals.

Advantageously, when a sample is clamped between the upper and lower frames and it is in contact with the first, the second, and the third secondary seals, the fourth channel connected to pumping means via the third channel enables to improve the tightness at the sample periphery to limit the above-mentioned lateral permeation phenomenon.

Possibly, to allow a more homogeneous suction by the fourth channel into the area defined by said secondary seals, the fourth channel may comprise a groove formed on the front surface of the lower frame of the sample holder between the first and the fourth secondary seals. Preferably, the groove surrounds the first secondary seal.

The present application also relates to a permeation measurement device comprising a permeation cell such as described hereabove, comprising a channel connecting the downstream chamber to a detection device located outside of the cell, said device being capable of detecting the presence and the quantity of a target gas originating from the upstream chamber of said cell.

The present application also relates to a method of installing a sample in an above-described removable support, comprising according to a first step sufficiently taking away the upper and lower frames to enable a sample to close the through opening of the lower frame, and then, according to a second step, holding the rear surface of the upper frame at closest to the sample via the removable sample holder assembly means. Thus, the sample is held between the two frames, which enables to displace the sample without requiring to directly grasp it. The removable sample holder thus enables to preserve the integrity of the sample on installation thereof in a permeation cell.

Preferably, the sample is in contact with the first and/or with the second and/or with the third primary seals to improve the tightness between the sample and the upper frame and/or the lower frame.

Possibly, a porous support may be arranged between the lower frame and the sample to mechanically support the sample during permeation measurements.

The removable sample holder comprising the sample may then be placed in a permeation cell such as described hereabove, by positioning according to a first step the rear surface of the lower frame in contact with the first and/or the second and/or the third and/or the fourth primary seals and so that the through opening of the lower frame is opposite the opening connecting the downstream chamber to the upstream chamber, and then, according to a second step, by means of the cell assembly means, pressing the rear surface of the lower frame of the sample holder against at least the first primary seal.

BRIEF DESCRIPTION OF THE DRAWINGS

The way in which the described embodiments may be implemented and the resulting advantages will better appear from the following non-limiting embodiments, in relation with the accompanying drawings, among which.

The drawings comprise orthogonal reference frames for a better understanding thereof.

DETAILED DESCRIPTION

Figure 3A:
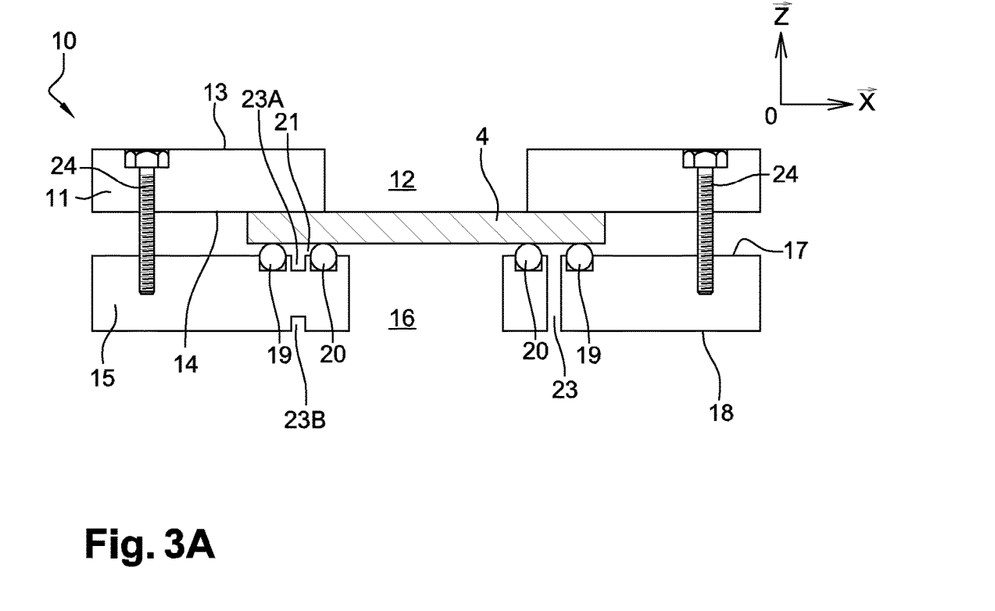
FIG. 3A is a simplified front view of a first embodiment of a sample holder.
Figure 3B:
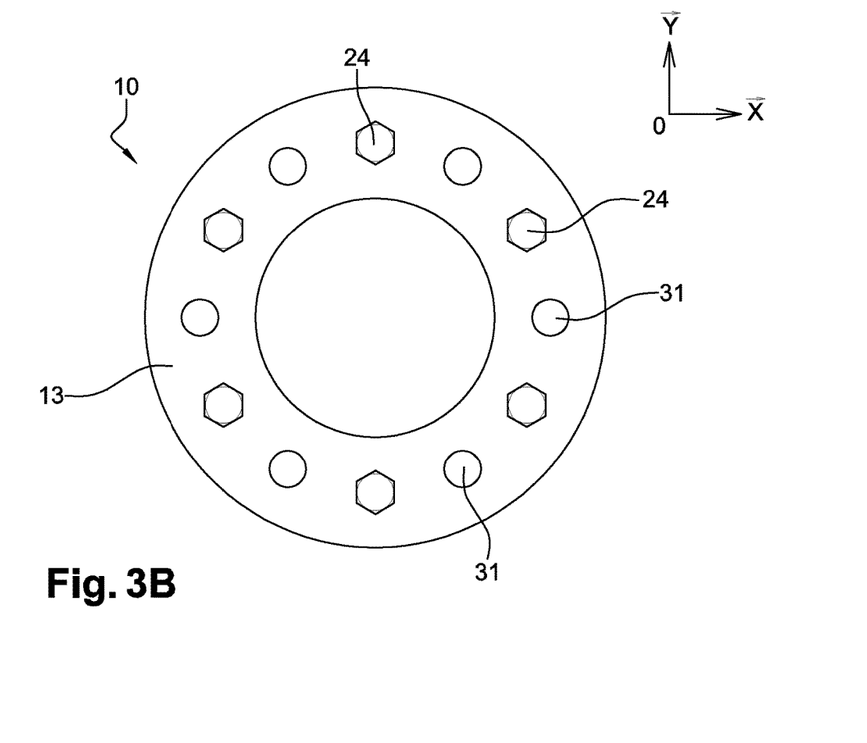
FIG. 3B is a simplified top view of the first embodiment according to FIG. 3A.

FIGS. 3A and 3B show a first embodiment of a removable sample holder (10). It comprises an upper frame (11) comprising a through opening (12), connecting a front surface (13) to a rear surface (14). It also comprises a lower frame (15) comprising a through opening (16) connecting a front surface (17) to a rear surface (18).

The front surface of lower frame (15) comprises a first O-ring seal (19) which surrounds the through opening (16). This first seal (19) surrounds a second O-ring seal (20) to define a first confined space (21) or area, between a sample (4) held between the two frames (11, 15), the two seals (19, 20), and the lower frame (15). The lower frame (15) comprises at the level of its front surface (17) a first groove (22A) coaxially formed between the seals.

A first channel (23) of the sample holder connects the rear and front surfaces of the lower frame (15). It comprises a first groove (23A) formed in the front surface (17) of the lower frame, and a second groove (23B) formed in the rear surface (18) of said frame. The second groove may be coaxial to the through opening (16). As a variation, the second groove is formed sideways with respect to the opening (16), which enables to use sample holders having different dimensions with respect to the cells.

The sample holder (10) comprises screws (24), for example, six, enabling to firmly hold the sample (4) between the two frames. The screws (24) and the corresponding threaded holes formed in the frames thus enable to simply assemble the sample holder by placing the frame openings opposite each other, and to disassemble the sample holder to sufficiently take away the frames from each other to place the sample, for example, by disengaging them from each other. The sample closes the through openings (12, 16). The screws also enable to compress the O-ring seals (19, 20) present between the sample and the lower frame to improve their tightness properties.

Advantageously, the first channel (23) of the sample holder may enable pumping means (not shown) to pump or to inject a neutral gas from or into the confined space (21). The first groove (22A) further allows a more homogeneous pumping between the two seals (19, 20).

Figure 4:
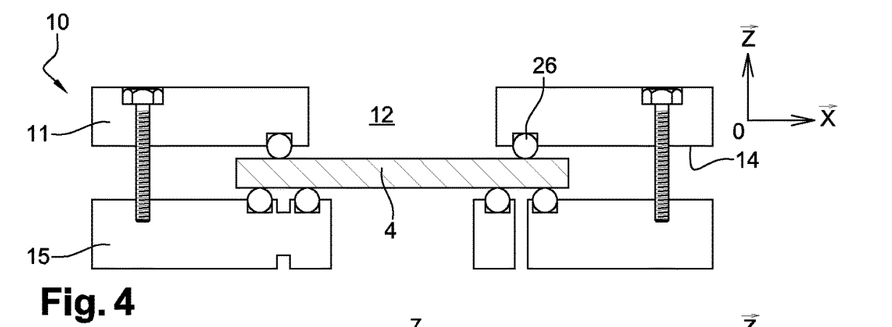
FIG. 4 is a simplified front view of a second embodiment of a sample holder.

FIG. 4 shows a second embodiment, which differs from the previous example by the presence of a third O-ring seal (26) flush with the rear surface (14) of the upper frame (11). This third seal surrounds the through opening (12) and is positioned to be in contact with a sample (4) clamped between the frames (11, 15).

Figure 5:
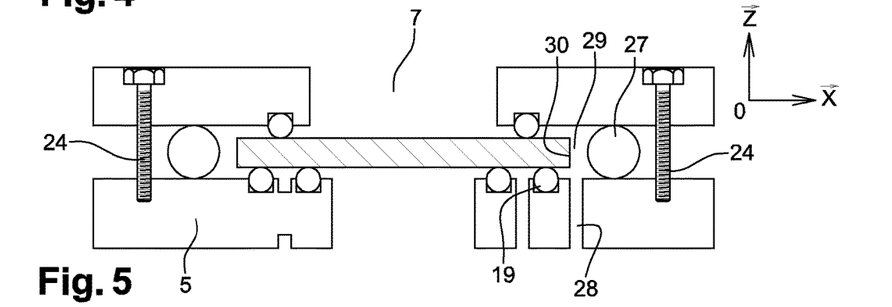
FIG. 5 is a simplified front view of a third embodiment of a sample holder.

FIG. 5 illustrates a third embodiment, additionally comprising, as compared with the second example, a fourth O-ring seal (27) in contact with the two frames when they are held together via screws (24). This fourth seal may be rigidly attached to one of the frames. The lower frame (15) comprises a second channel (28) of the sample holder parallel to the first channel (23) and emerging between the first seal (19) and the fourth seal (27).

Advantageously, this embodiment enables to define a second confined space (29) around the edge (30) of the sample (4). More specifically, this space is defined by the first, the third, and the fourth seals located between the two frames.

The seal dimensions are selected to be able to tightly isolate the edge (30) of the sample from a target gas (7) present above the lower frame (15). In the same way as for the first channel, the second channel (28) may enable pumping means to inject an inert gas into or to lower the pressure in this second confined space (29).

Figure 6:
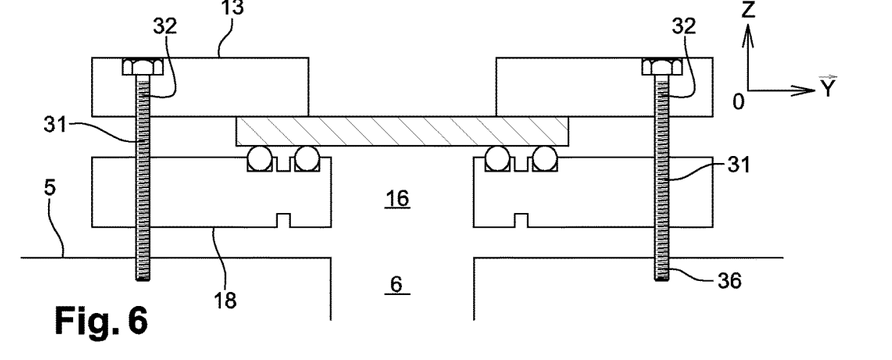
FIG. 6 is a simplified profile view of the first embodiment.

The above-described sample holders comprise six bores (31) such as shown in FIG. 3B and FIG. 6, connecting the front surface (13) of the upper frame (11) to the lower surface (18) of the lower frame (15). The bores are homogeneously distributed along the periphery of the sample holder (10). They enable screws (32) to hold, for example, the first sample holder close to the bottom (5) of an upstream chamber belonging to a permeation cell such as described hereabove. The screws allow an accurate and fast positioning of the sample holder in the downstream chamber of the cell due to threaded holes (36) present in the bottom (5) of the upstream chamber. They also enable to easily disassemble the sample holder from the cell to take the sample holder out of the cell.

Figure 7:
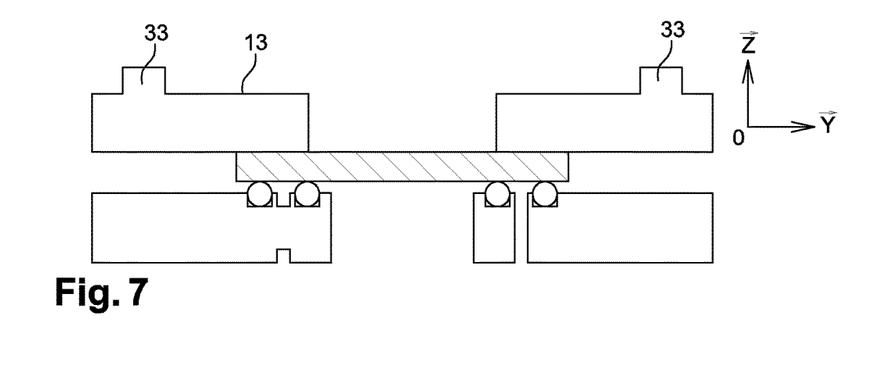
FIG. 7 is a simplified front view of another embodiment of a sample holder.
Figure 12:
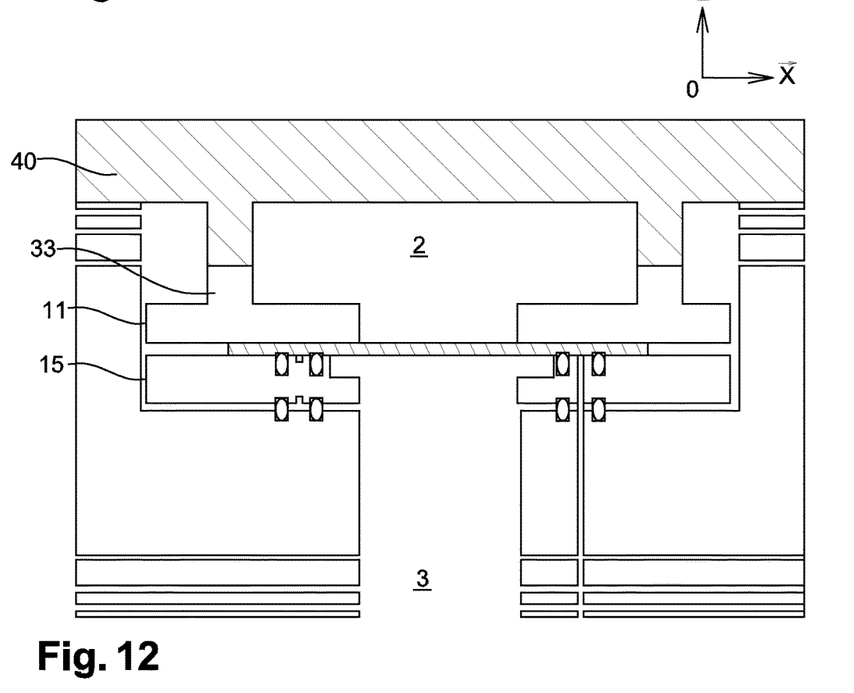
FIG. 12 is a transverse simplified cross-section view of a permeation device, comprising a sample holder shown in FIG. 7.

According to a more advantageous alternative embodiment shown in FIG. 7, the front surface (13) of the upper frame comprises a strapping (33) positioned and sized to cooperate with a device (40) for closing the upstream chamber (2) shown in FIG. 12. When the chamber is closed, the closing device presses and holds the sample holder against the bottom (5) and the upper and lower frames towards each other. The strapping enables to homogeneously distribute the pressure on the sample holder (10). In this case, screws enabling to hold together the frames of the sample holder may be replaced with holding or positioning pins due to the fact that the clamping is applied by the closing device. In other words, the sample holder may then comprise no screws such as mentioned hereabove.

The present application also relates to a permeation cell (1) capable of cooperating with one of the above-described sample holders.

Figure 8:
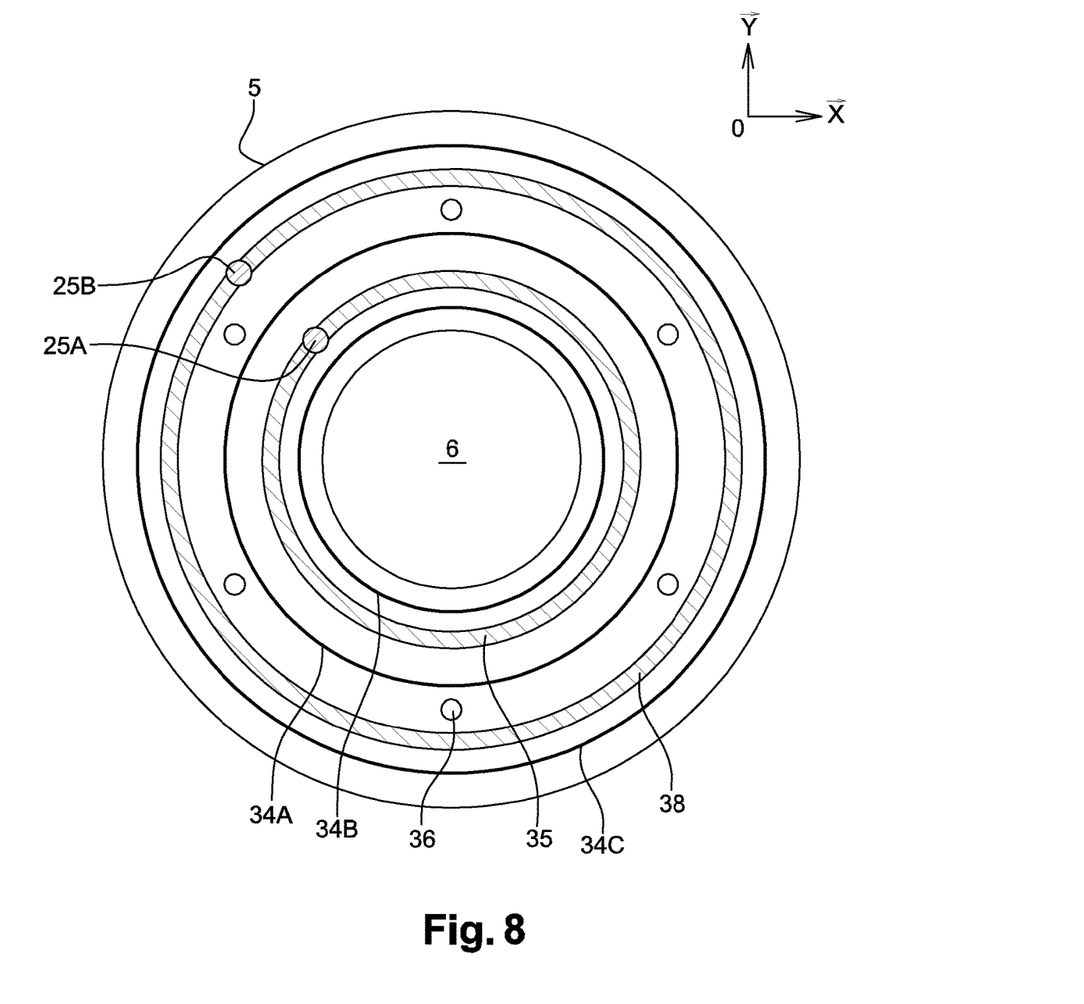
FIG. 8 is a simplified top view of the bottom of the upstream chamber of a permeation cell.

According to a first embodiment illustrated in FIG. 8, the permeation cell (1) comprises an upstream chamber (2) delimited by a bottom (5), said bottom comprising:

at least one first primary seal (34A) and one second primary seal (34B) both surrounding an opening (6);

a first groove (35) formed in the bottom of the chamber between the two primary seals coaxially with said opening;

a first pumping channel (25A) emerging into the groove (35) and connected to pumping means (not shown); and threaded holes (36), for example, six, formed in the bottom (5).

Figure 9:
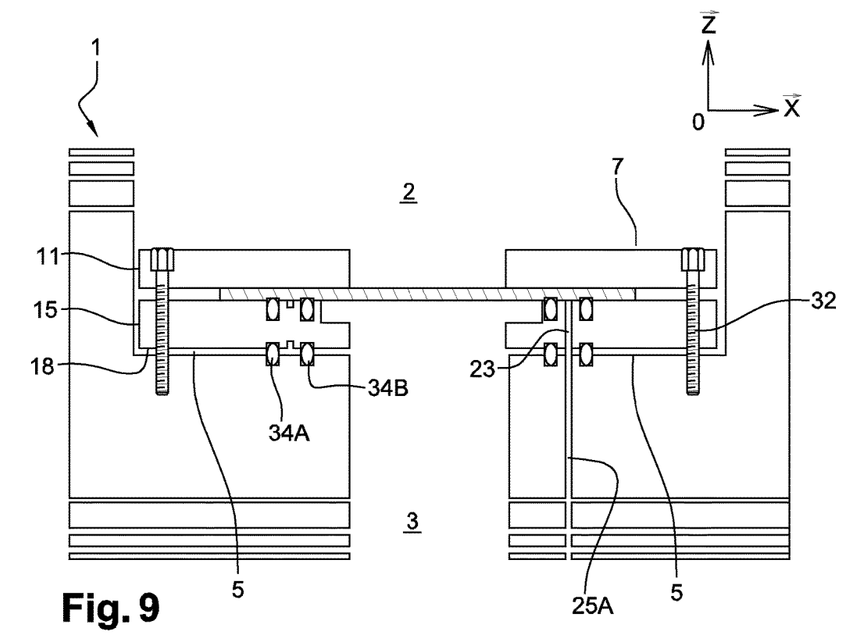
FIG. 9 is a transverse simplified cross-section view of a permeation cell, comprising a sample holder shown in FIG. 3A.

The threaded holes are arranged in the bottom (5) of the upstream chamber to allow a fast and accurate positioning of the sample holder by means of the above-mentioned screws (32) (FIG. 9).

The primary seals (34A, 34B) are positioned so that the first channel (25A) emerges between said seals. Pumping means connected to the first channel (25A) may then inject a neutral gas or lower the pressure in the first confined space (21) of the above-defined sample holder (10), via the first channel (23) of the sample holder.

To also allow the pumping of the second confined space (29) in the above-described sample holder (FIG. 5), the bottom (5) may comprise:

a third primary seal (34C) surrounding the other primary seals (34A, 34B);

a second groove (38) formed in the bottom (5) between the second and the third primary seals;

a fourth pumping channel (25B) emerging into the second groove (38) (FIG. 8).

Figure 10:
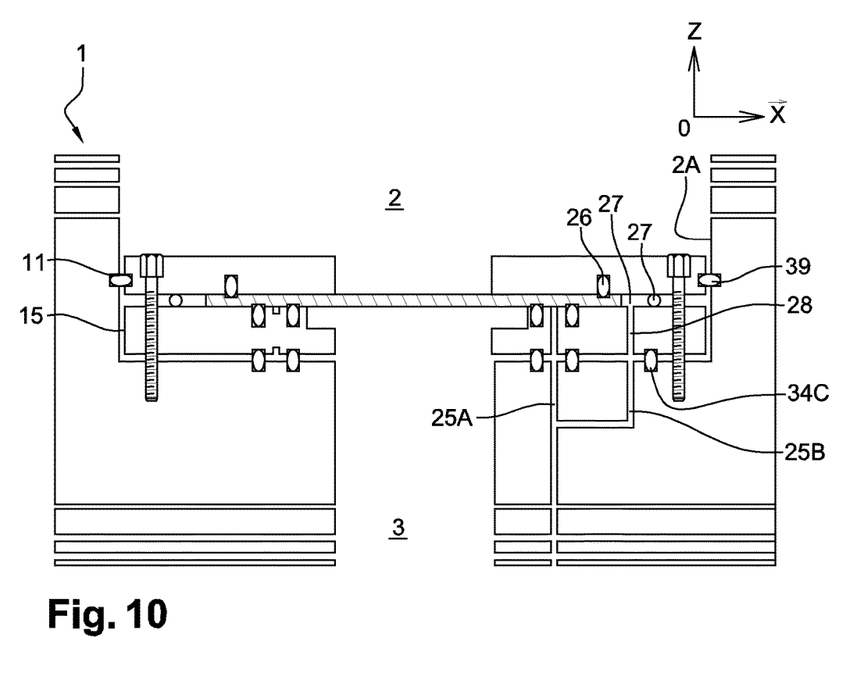
FIG. 10 is a transverse simplified cross-section view of a permeation cell, comprising a sample holder shown in FIG. 4.

As previously, the first and the third primary seals are positioned so that the fourth channel (25B) of the sample holder emerges between said seals. Thus, pumping means connected to the fourth channel (25B) may inject a neutral gas or lower the pressure in the second confined space (29) of the sample holder (FIG. 10), via the second channel (28) of the sample holder.

Figure 11:
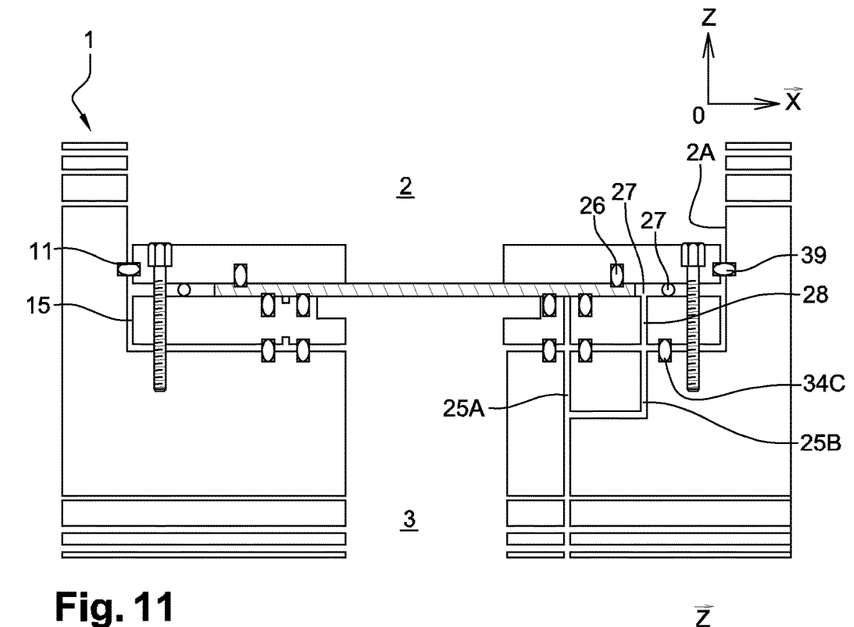
FIG. 11 is a transverse simplified cross-section view of a permeation cell, comprising a sample holder shown in FIG. 5.

According to an alternative embodiment, a lateral wall (2A) of the upstream chamber comprises a lateral O-ring seal (39) inscribed within a plane parallel to the bottom (5) (FIG. 11). The lateral seal (39) is positioned to be in contact with the upper frame (11) when sample holder is placed in the upstream chamber. This embodiment is particularly relevant during the use of a sample holder such as shown in FIG. 4. Indeed, the second and the third seals of the sample holder and the lateral seal tightly isolate the edge (30) of the sample (4). Thus, the previously-mentioned lateral permeation phenomenon is limited.

According to a variation, the bottom (5) of the upstream chamber may comprise no threaded holes. The sample holder is then held against the primary seals and possibly the secondary seal via a device (40) for closing the chamber (FIG. 11).

According to another variation, the sample holder shown in FIG. 7 may be held against the primary seals (34A, 34B) via a device (40) for closing the upstream chamber (2) of a permeation cell. The strapping (33) present on the front surface of the upper frame may cooperate with the closing device so that said device exerts a force on the sample holder, capable of holding it on the bottom (5) of the upstream chamber (2). Thereby, the installing of the sample holder (4) is even faster since it is no longer necessary to perform any screwing step such as described hereabove.

Advantageously, the closing device may cooperate with a threading (not shown) present on the outer surface of the permeation cell, to enable to apply a progressive force to the sample holder to press it against the primary seals (34A, 34B) present on the bottom (5).

The presently described embodiments also relate to a method of installing a sample holder (10) such as previously described on the bottom (5) of an upstream chamber (2) of an above-mentioned permeation cell. This method comprises a first step comprising placing in contact the rear surface of the lower frame of the sample holder with the primary seals (34A, 34B, 34C) of the downstream chamber, so that said seals surround the first channel (23) of the sample holder and that the through opening (16) is positioned opposite the opening (6). A second step comprises activating pumping means connected to the first channel (25A) (not shown) to inject an inert gas or to pump a gas present in the first confined step (21).

As a variation, the method may comprise, between these two steps, a step of holding the sample holder close to the bottom (5). This step may comprise screwing the screws (32) in threaded holes (36) present at the bottom (6), or screwing the closing device (40) of the upstream chamber to press the sample holder against the primary seals (34A, 34B).

An above-described sample holder has the advantage of positioning the sample (4) between its two frames (11, 15) outside of the permeation cell (1). Thereby, the manipulations to hold a fragile sample on a support are no longer performed inside of the permeation cell. Installing the sample in the upstream chamber is thus easier and faster. The sample holder may be held at the bottom of the downstream chamber by simple screwing in dedicated housings (FIGS. 9 and 10) or by the device (40) for closing the upstream chamber (FIG. 11). The time of exposure of the downstream chamber to the target gas is then decreased on installing and retrieval of the sample.

The cooperation between the sample holder and the measurement device thus allows a faster and simpler closing of the opening (6) by the sample (4). Thereby, the opening time of the two chambers (2, 3) is decreased to its minimum.

Advantageously, at least two sample holders are alternately used in a permeation device so that the opening (6) is permanently closed by one of the sample holders except, of course, for the phases of assembly and disassembly thereof.

Another advantage linked to the sample holder is that its introduction and its retrieval may be performed at will into and from the upstream chamber (2) without requiring, for this purpose, to directly manipulate it. In other words, the free surface of the sample is kept intact on retrieval thereof out of the permeation cell. It is then possible to carry out tests of different natures between two series of permeability measurements, while preserving the structure and the surface state of the sample. The sample holder thus enables to perform permeativity measurements on fragile films which are repeatable.

The channels of the lower frame (22A, 22B), the seals (19, 20, 26, 27) surrounding them, and the pumping means (25) belonging to the measurement device (1) enable to provide an optimized tightness between the edge (30) of the sample and the downstream chamber in fast and certain fashion. Indeed, when the lower frame is in contact with the seals (34, 37) present at the bottom (5) of the upstream chamber, the pumping means may rapidly inject an inert gas or pump out a gas present between the seals to provide an optimized tightness between the sample and the supports, on the one hand, and between the sample holder and the bottom (5) of the downstream chamber (2), on the other hand. It is thus possible to degas the sample with the sample holder, in a step prior to the permeability measurement.

The combination between a sample holder and a measurement device also enables to limit the lateral permeation phenomenon since the edge (30) of the sample is advantageously tightly isolated from the target gas (7) present in the upstream chamber due to the above-mentioned seals. Thus, the sample surface exposed to the target gas is accurately known, it corresponds to the surface of the through opening (12). The measurements are no longer distorted by the lateral permeation phenomenon.

What is claimed is:

1. A permeation cell capable of measuring the permeation of a target gas through a sample comprising:
   an upstream chamber capable of containing the target gas and delimited by a bottom;
   a downstream chamber capable of being in fluidic communication with a target gas detection device;
   a main channel connecting the downstream chamber to the upstream chamber and emerging into the bottom of the upstream chamber;
   a first primary seal in contact with the bottom of the upstream chamber and surrounding the opening;
   fixing means for fixing the sample at the bottom of the upstream chamber, the fixing means comprising a sample holder which is removable, so that it can be detached from the cell, the sample holder comprising:
      an upper frame provided with a front surface and with a rear surface connected by a through opening;
      a lower frame capable of being taken away from the upper frame, provided with a front surface and with a rear surface connected by a through opening;
      means for assembling the sample holder settable between an assembled state of the sample holder where the rear surface of the upper frame and the front surface of the lower frame are pressed towards each other with the openings of the upper and lower frames facing each other, to hold the sample in the sample holder opposite said openings, and a disassembled state of the sample holder where the upper and lower frames are capable of being taken away from each other to allow the installing and the retrieval of the sample from the sample holder;
   means for assembling the cell, settable between a state where the rear surface of the lower frame of the sample holder is pressed against the first primary seal and a state where the sample holder is free,
   wherein the sample holder comprises a first secondary seal showing on the front surface of the lower frame of the sample holder, the first secondary seal surrounding the through opening of the lower frame of the sample holder;
   and wherein the lower frame of the removable sample holder comprises:
      a second secondary seal showing on the front surface of the lower frame of the sample holder and surrounding the through opening of the lower frame of the sample holder, the second secondary seal being surrounded with the first secondary seal;
      the front surface and the rear surface of the lower frame of the sample holder are connected by a second channel emerging between the two secondary seals.

2. The permeation cell of claim 1, wherein the means for assembling the sample holder comprise at least two screws crossing the front and rear surfaces of the upper frame of the sample holder and the front surface of the lower frame of the sample holder.

3. The permeation cell of claim 1, wherein the means for assembling the cell comprise at least two screws crossing the front and rear surfaces of the upper and lower frames of the sample holder, said screws being screwed in threaded holes, formed in the bottom of the upstream chamber.

4. The permeation cell of claim 1, wherein the means for assembling the cell comprises means for pressing the front surface of the upper frame of the sample holder to hold the rear surface of the lower frame of the sample holder pressed against the first primary seal.

5. The permeation cell of claim 1, wherein a second primary seal is in contact with the bottom of the upstream chamber, the second primary seal surrounding the opening and being surrounded with the first primary seal.

6. The permeation cell of claim 5, wherein a first channel emerges into the bottom of the upstream chamber between the first and the second primary seals.

7. The permeation cell of claim 6, wherein the first channel comprises a groove formed between the first and the second primary seals.

8. The permeation cell of claim 1, wherein the second channel comprises a groove formed on the front surface of the lower frame of the sample holder and between the two secondary seals.

9. The permeation cell of claim 1, wherein a third channel emerges into the bottom of the upstream chamber between the first primary seal and a lateral wall delimiting the upstream chamber and its bottom.

10. The permeation cell of claim 9, further comprising a third primary seal in contact with the upper frame of the sample holder and the lateral wall of the upstream chamber, the sample holder comprising a third secondary seal flush with the rear surface of the upper frame of the sample holder and surrounding the through opening of the upper frame of the sample holder.

11. The permeation cell of claim 9, further comprising a third primary seal in contact with the bottom of the upstream chamber and the rear surface of the lower frame of the sample holder, the third primary seal surrounding the third channel and the first primary seal, the removable sample holder comprising:
   a third secondary seal flush with the rear surface of the upper frame and surrounding the through opening of the upper frame;
   a fourth secondary seal in contact with the rear surface of the upper frame of the sample holder and the front surface of the lower frame of the sample holder, the fourth secondary seal surrounding the third secondary seal;
   a fourth channel emerging between the first and the fourth secondary seals and between the first and the third primary seals.

12. The permeation cell of claim 9, wherein the third channel comprises a groove formed in the bottom of the upstream chamber between the first primary seal and the lateral wall delimiting the upstream chamber and its bottom.

* * * * *